United States Patent
Wine et al.

[11] Patent Number: 5,956,760
[45] Date of Patent: Sep. 28, 1999

[54] FACIAL SUNSHIELD WITH HINGED VISOR/CAP

[76] Inventors: Peggy M. Wine; Jan W. Wine, both of 19501 Ranch La. #108, Huntington Beach, Calif. 92648

[21] Appl. No.: 08/349,675

[22] Filed: Dec. 5, 1994

[51] Int. Cl.⁶ .................................................. A41D 13/00
[52] U.S. Cl. ................................................ 2/9; 2/7; 2/206
[58] Field of Search .................. 2/6.3, 6.5, 6.7, 2/9, 10, 7, 8, 15, 173, 206, 424, 453

[56] References Cited

U.S. PATENT DOCUMENTS

| | | | |
|---|---|---|---|
| D. 274,385 | 6/1984 | Newcomb | D2/234 |
| 1,176,313 | 3/1916 | Pfund | 2/8 |
| 2,037,772 | 4/1936 | Everett | 2/12 |
| 2,385,405 | 9/1945 | Crowther | 2/12 |
| 2,395,297 | 2/1946 | Shock | 2/14 |
| 2,669,717 | 2/1954 | Diggs | 2/9 |
| 2,729,820 | 1/1956 | Anderson | 2/9 |
| 3,298,031 | 1/1967 | Morgan | 2/9 |
| 3,705,760 | 12/1972 | Langendorfer | 351/44 |
| 4,541,125 | 9/1985 | Phillips | 2/10 |
| 4,786,159 | 11/1988 | Piazza | 351/132 |
| 4,944,039 | 7/1990 | Dietrich | 2/13 |
| 5,012,527 | 5/1991 | Michel | 2/9 |
| 5,012,528 | 5/1991 | Pernicka | 2/10 |
| 5,187,502 | 2/1993 | Howell | 2/6.3 |
| 5,220,689 | 6/1993 | Miller | 2/12 |
| 5,448,780 | 9/1995 | Gath | 2/424 |

*Primary Examiner*—Diana L. Biefeld

[57] ABSTRACT

A sunshield comprised of a large lens assembly (32) providing protection for the face and head from solar radiation wind, snow, flying objects, caustic liquids, water, and other forces. A one piece lens (12) is comprised of a tinted transparent plastic coated with ultraviolet radiation blocking coating. Lens (12) can be comprised of optically correcting material to accommodate wearer's vision. Lens assembly (32) flips up over the front of the head to act as a visor by protecting the front of the head and shading the forehead or to enable lens assembly (32) to be out of the line of sight without removal. Lens assembly (32) can be adjusted to a comfortable distance from the wearer's face and to accommodate wearing of ordinary eyeglasses.

12 Claims, 4 Drawing Sheets

FACIAL SUNSHIELD WITH HINGED VISOR/CAP

BACKGROUND—FIELD OF THE INVENTION

This invention relates generally to protective devices for shielding the face and head from solar radiation, wind, water, snow, flying objects, caustic liquids, and other forces. Specifically, it relates to a facial sunshield that provides more effective protection against these forces.

BACKGROUND—DISCUSSION OF PRIOR ART

Sunshields currently used to protect the face and head of people being exposed to the sun are hats, caps, visors, and ultraviolet blocking sunglasses. Due to raised health conscienceness and increased leisure time, more people are spending increasing amounts of time outdoors, leading to exposure to harmful ultraviolet radiation. With more knowledge gained regarding the harmful effects of ultraviolet radiation, protective devices gain importance.

Hats, caps, and visors protect the area near the top of the head but do not protect the front or side of the face and do not directly shield the eyes. Ultraviolet blocking sunglasses protect the eyes and the area immediately surrounding the eyes. Larger sportglasses may protect more of the facial area but do not cover the entire facial area.

With recent concern for the health hazards of extended periods in the sun, many products are available to help protect our faces from the sun's rays. Sunglasses are used to protect the eyes from the sun. The glasses composed of ultraviolet protective lenses do an effective job but do not protect the face aside from the immediate area around the eyes and eyelids.

A number of attempts have been made to provide facial protection above that provided by ordinary sunglasses. U.S. Pat. No. 5,220,689 to Miller (1993) shows sportglasses composed of two lenses with a separate nosepiece and exposed lips, mouth, chin, and top of the face. These sportglasses leave the entire forehead area exposed. These sportglasses do not cover the total facial area and attach similar to conventional glasses. This patent specifically warns against covering the whole front of the face due to "impaired breathing and speaking". These attach to the ears rigidly as do normal glasses and do not provide any protection to the top or front of the head or act as a visor. These do not adjust for the distance of the lens to the face and do not rotate up. In addition, these cannot be worn with conventional glasses.

U.S. Pat. No. 5,012,528 to Pernicka et al. (1991) shows a visor attachment for safety helmets. This device is not intended for use as a sunshield and is used in conjunction with a safety helmet and is not versatile.

U.S. Pat. Nos. 2,037,772 to Everett et al (1936) and 4,786,159 to Piazza et al (1988) show eyeglasses of average size with nosepieces which shield the nose. However the extra coverage provided over simple sunglasses is minimal.

U.S. Pat. Nos. 2,385,405 to Crowther (1945), 2,395,297 to Shock (1946), 3,705,760 to Langendorfer et al (1972), and 5,012,527 to Michel (1991) show goggles which are fitted closely with the face. They wrap around the eyes and cover the cheeks down to the level at about the base of the nose. Some cover the nose, while some do not, but all leave the sides or cheeks of the face exposed.

U.S. Pat. No. Design 274,385 to Newcomb (1984) shows a face shield which attaches to ski goggles with hook and loop fasteners. The shield covers the nose, upper lip, and under part of the eyes, but not the cheeks. Because the shield must be used with ski goggles, it is not at all versatile.

U.S. Pat. Nos. 2,669,717 to Diggs (1954), 3,298,031 to Morgan (1967) and 4,944,039 to Dietrich (1990) show face shields that are attached to ordinary eye glasses. Intended for use in workshops or industrial situations for protection against flying debris or caustic liquids, the shields hang from the glasses to cover the whole front of the face down to the chin, but not the sides or cheeks.

All these devices cover portions of the face or shield the eyes but none cover the entire front of the face including the forehead, eyes, nose, cheeks, and chin. None are versatile enough to act as a visor or protect the top of the head.

OBJECTS AND ADVANTAGES

Several objects and advantages of the present invention are:

(a) to protect the eyes, front, and sides of the face and forehead from sun radiation, wind, water, and dust.

(b) to provide a swing up shield that will turn into a visor to shield the top of the head and front top of the face.

(c) the one piece lens is less complicated and inexpensive to manufacture compared to two piece lens assemblies.

(d) the one piece lens provides substantially more coverage than two (or more) piece lens shields, including covering the nose, mouth, forehead and face sides.

(e) the swing up shield provides convenience when shielding is not desired, as in entering a shaded building. The shield does not have to be removed to see in shaded areas, to converse, or to eat.

(f) the sunshield is aesthetic to the eye and compliments the wearer.

(g) the one piece lens provides unobstructed viewing.

(h) the lens can be adjusted for a comfortable distance from the wearer's face and can be worn over conventional glasses.

(I) the one piece lens can be optically correcting if desired to accommodate the wearer's vision.

Further object and advantages are to provide a facial sunshield that is aesthetic, provides protection from the elements of the entire face, is convenient to use as a shield or a cap, and easy and inexpensive to manufacture. Further objects and advantages of my invention will become apparent from a consideration of the drawings and ensuing description.

DRAWING FIGURES

Figure 1:
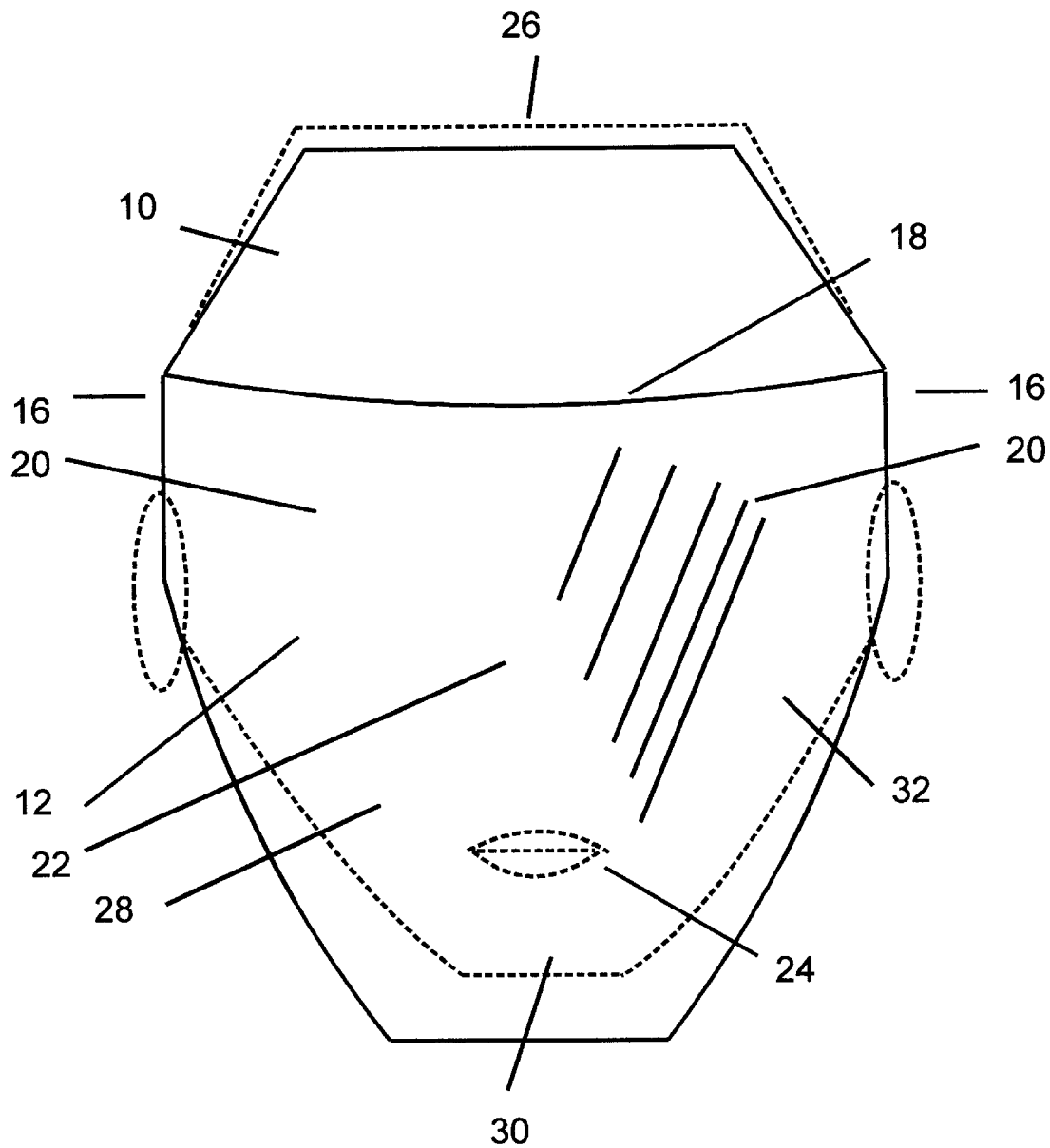
FIG. 1 is a front view of the sunshield.

REFERENCE NUMERALS IN DRAWINGS 10 top cap
12 lens
14 headstrap
16 hinges with friction mechanism
18 forehead
20 eyes
22 nose
24 mouth
26 head 28 face
30 chin
32 lens assembly
34 adjustment hooks
36 lens adjustment slot Description—FIG. 1

A typical embodiment of the present invention is shown in FIG. 1 (front view). The sunshield has a large lens 12 of tinted transparent material covering the face 28 of the wearer. Lens 12 can be rotated and flipped up. Lens 12 can also be adjusted in the distance from face 28 to ensure comfort for the wearer. This front and back adjustment will provide a comfortable distance of lens 12 from the wearer's nose 22, mouth 24, or other facial features. In the preferred embodiment, lens 12 is a ultraviolet coated polycarbonate plastic. However lens 12 could be made of any tinted plastic that is transparent and that can be formed or molded into shape. A top cap 10 piece is molded as part of lens 12 or as an additional piece attached to lens 12 and covers the front of wearer's head 26 and forehead 18. Top cap 10 can be transparent or opaque since it is out of direct view of the wearer's eyes 20. Lens 12 is curved in shape to conform with face 28 and is sufficiently large to cover forehead 18, eyes 20, nose 22, mouth 24, and chin 30.

Hinges 16 are used to allow lens 12 and top cap 10 assembly to swing up to expose face 28 for eating or to view the scene without having to look through tinting or to use as a visor. Hinges 16 contain a ratchet or friction mechanism to hold lens assembly 32 in any rotated position. Lens 12 and hinge 16 assembly contain a lens adjustment slot 36 to allow adjusting lens 12 closer or farther from face 28. This provides a comfortable distance for lens 12 from face 28, fits various head 26 sizes, and accommodates the wearing of conventional glasses.

Figure 2:
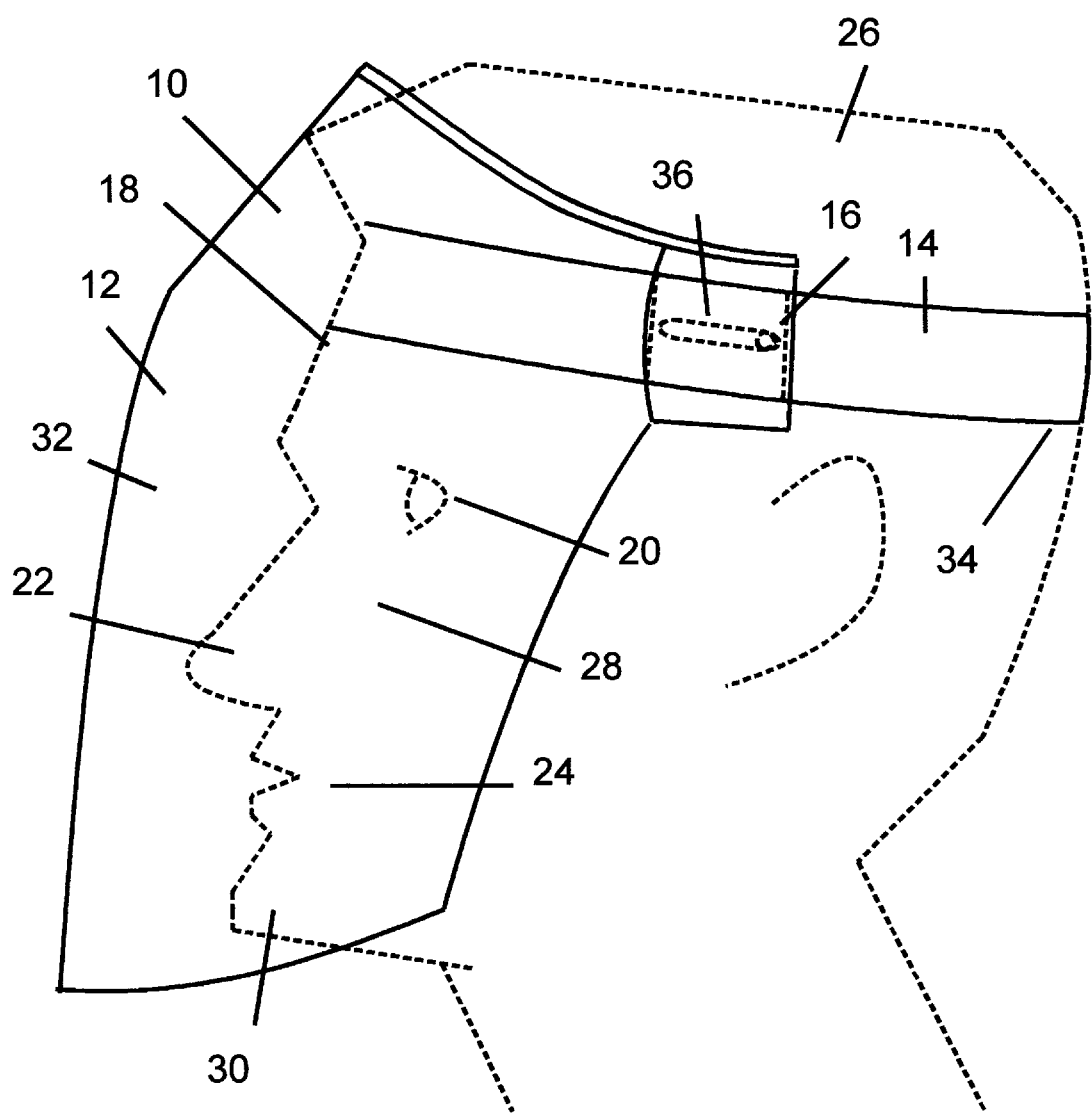
FIG. 2 is a left side view of the sunshield.

Description—FIG. 2

FIG. 2 is a left hand view of the sunshield of FIG. 1. The left and right views are symmetrical.

Lens 12 is sufficiently large to cover eyes 20 and a large portion of the sides of face 28 and forehead 18. In the preferred embodiment, lens 12 is ultraviolet coated to block harmful radiation. Lens 12 is curved in shape to conform with face 28 and is sufficiently large to cover forehead 18, eyes 20, nose 22, mouth 24, and chin 30. Lens 12 uses hinges 16 to allow lens 12 and top cap 10 assembly to rotate and a friction or ratchet mechanism holds lens assembly 32 at any desired rotated position. Lens adjustment slot 36 enables lens 12 to be adjusted to a comfortable distance from face 28. Lens assembly 32 is attached to wearer's head 26 by an adjustable flexible head strap 14. Flexible headstrap 14 surrounds the top of wearer's head 26 to hold the sunshield securely. Headstrap 14 uses a quick attachment technique such as adjustment hooks 34 into various holes in headstrap 14 or a hook and loop method. Headstrap 14 is adjustable to fit various head 26 sizes and holds snugly to keep the sunshield in place during movement by the wearer and in windy conditions.

Figure 3:
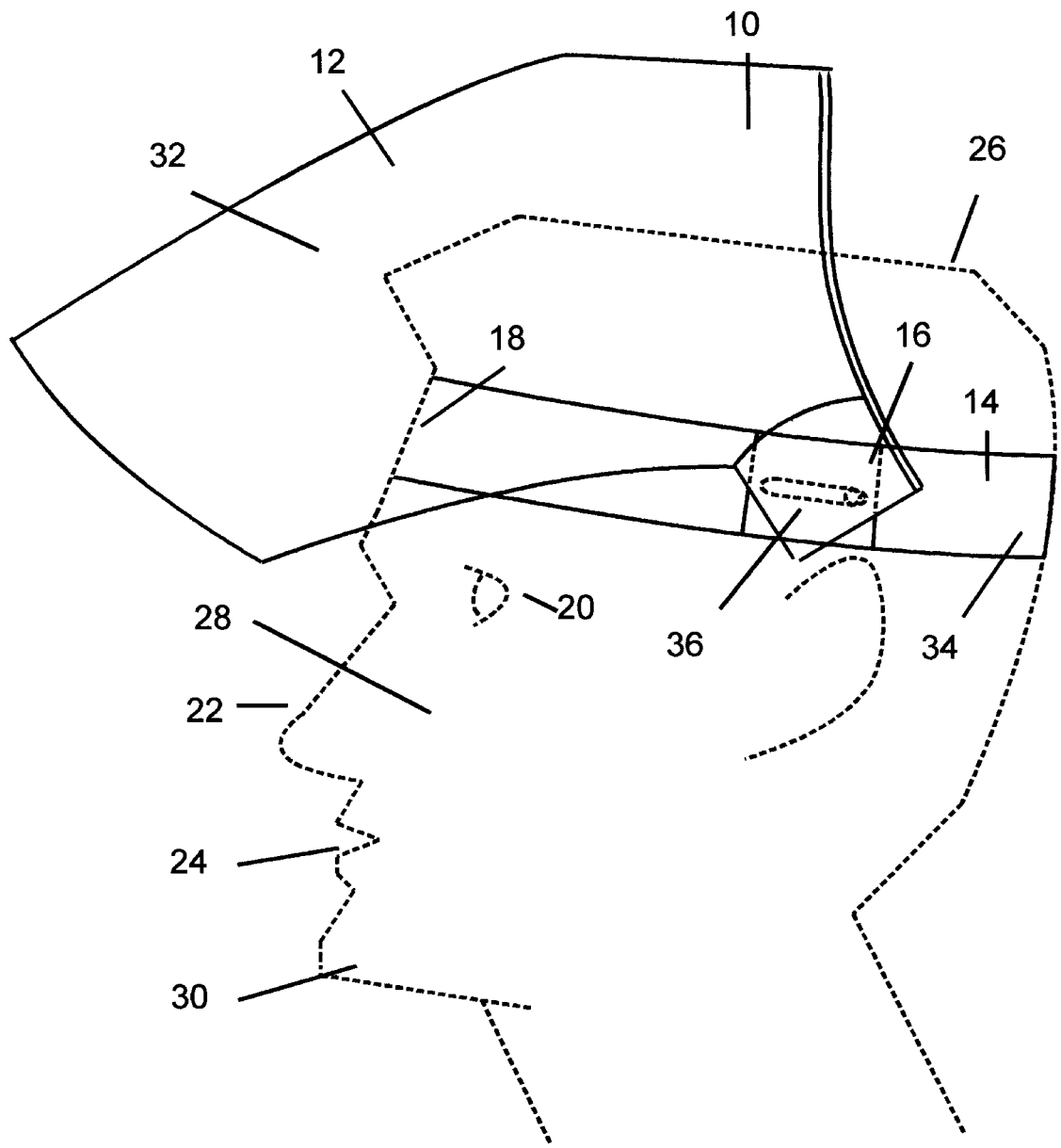
FIG. 3 is a left side view of the sunshield in the raised position.

Description—FIG. 3

FIG. 3 is another left hand view with lens assembly 32 in a flipped up mode. The left and right views are symmetrical.

Lens assembly 32 uses hinges 16 to allow lens 12 and top cap 10 assembly to rotate up and over head 26. Hinges 16 uses a friction mechanism or ratchet to hold lens assembly 32 in place in multiple or varying rotated positions. Lens adjustment slot 36 enables lens 12 to be adjusted to a comfortable distance from face 28. Top cap 10 is shaped to clear the top of wearer's head 26. Headstrap 14 fits around the front of head 26 at the top of wearer's forehead 18. Headstrap 14 uses a quick attachment technique such as adjustment hooks 34 into various holes in headstrap 14 or a hook and loop method. Headstrap 14 is adjustable to fit various head 26 sizes and holds snugly to keep the sunshield in place.

Figure 4:
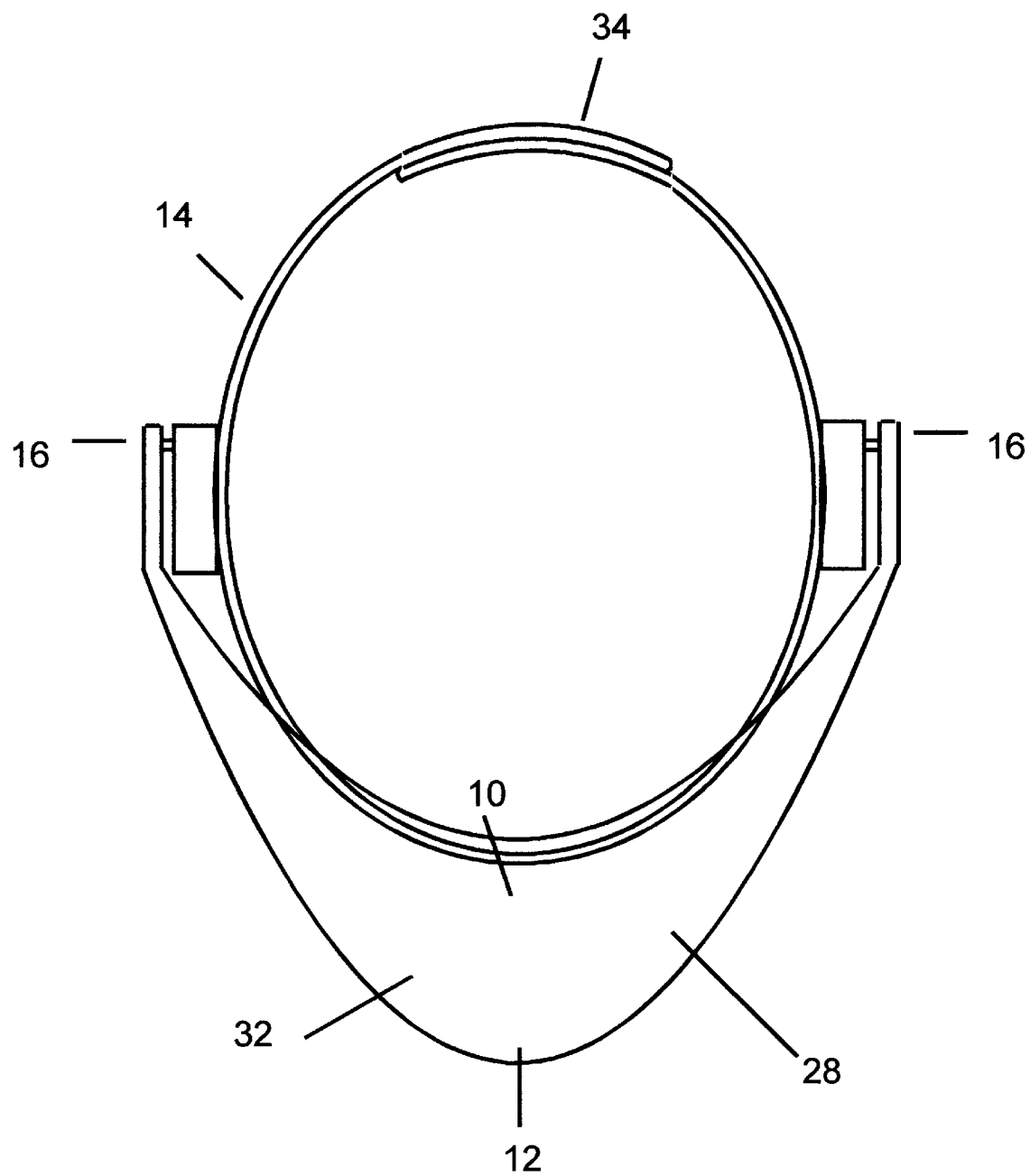
FIG. 4 is the top view of the sunshield.

Description—FIG. 4

FIG. 4 is the top view with lens assembly 32 in the rotated down position.

Top cap 10 covers the front portion of wearer's head 26 and forehead 18. Lens 12 is curved in shape to conform with face 28. Flexible headstrap 14 encircles head 26 with adjustment hooks 34 at the rear of head 26. Headstrap 14 holds lens assembly 32 securely to head 26.

From the description above, a number of advantages of my sunshield become evident:

(a) the sunshield protects a large area of the face with the eyes, front, and sides of the face and forehead protected from sun radiation, wind, water, and dust.

(b) the swing up feature of the sunshield turns the sunshield into a visor that protects the top of the head and front top of the face.

(c) the one piece lens is less complicated and less expensive to manufacture compared to two piece lens assemblies.

(d) the one piece lens provides more coverage than two (or more) piece lens shields, including covering the nose, mouth, forehead and face sides.

(e) the swing up shield provides convenience when shielding is not desired, as in entering shaded or darker areas. The swing up feature allows the wearer to speak or to eat easily without removing the sunshield.

(f) the sunshield is aesthetic to the eye and compliments the wearer.

(g) the one piece lens provides unobstructed viewing.

(h) the lens distance from the face can be adjusted allowing for different head and face sizes and to accommodate wearing of ordinary eyeglasses.

(l) the lens can be made optically correcting to accommodate the wearer's vision.

Operation—FIGS. 2 to 3

The manner of using the sunshield between the flipped down versus the flipped up position is to pull up on the lens assembly 32 to rotate around the hinges 16. Enough force is used to overcome the friction of the ratchet or friction mechanism 36 used to hold the lens assembly 32 in any desired angle.

To lower the lens assembly 32, push down on the lens assembly 32 to rotate around hinges 16 and to overcome the friction of hinge mechanism 16.

Pull or push lens assembly 32 to slide lens assembly 32 closer or farther from face 28 until a comfortable distance is achieved. Lens adjustment slot 36 allows adjusting lens 12 to accommodate wearing of ordinary eyeglasses.

SUMMARY, RAMIFICATIONS, AND SCOPE

Accordingly, the reader will see that the sunshield of the invention can provide superior protection to the eyes, face, and top of the head of the wearer while providing superior ease of use. The wearer can flip up the shield to use as a visor, to wear with normal sunglasses, to eat, or to see without the shield. Furthermore the sunshield has the additional advantages in that it permits an easy flip up of the shield to enable the wearer to see without the tinting of the shield, or to eat, or to talk without removing the shield from the head.

it permits wearing the shield flipped up as a visor.

it permits wearing the shield flipped up as a cap.

it protects the entire face from harmful solar radiation, blowing dust, or water including the eyes, cheeks, face front, nose, mouth, chin, and forehead.

it permits adjusting the shield to a comfortable distance from the face.

it permits wearing of ordinary eyeglasses together with the sunshield.

Although the description above contains many specificities, these should not be construed as limiting the scope of the invention but as merely providing illustrations of some of the presently preferred embodiments of this invention. For example, the shield can have other shapes, such as circular, square, rectangular, etc.; the lens curvature can be complex; the lens colors can be varied; the lens can have reflective coating; the lens can be clear;

Thus the scope of the invention should be determined by the appended claims and their legal equivalents, rather by the examples given.

We claim:

1. A facial sunshield comprising a one piece lens which is designed to curve around the top, front, and sides of a wearer's face, said lens sized to substantially cover the forehead, front, and sides of a wearer's face and a wearer's nose, mouth and chin, said lens having a curved upper portion generally designed to follow the angle of a wearer's forehead, said lens having curved side portions generally formed to shield a wearer's cheeks, said lens having a curved bottom portion formed to shield a wearer's mouth and chin generally extending down as far as a wearer's chin, said lens having a curved center portion formed to shield a wearer's eyes and nose, said lens having side edges generally designed to extend to a wearer's jaw line and formed to leave a wearer's ears uncovered, said lens having a top edge designed to extend generally to the top of a wearer's hairline, said lens having tinting for eye comfort, said lens having an ultraviolet radiation blocking coating to protect a wearer's face from harmful ultraviolet radiation.

2. The facial sunshield of claim 1 wherein said one piece lens is attached to a headband and hinging means which enables said one piece lens to swivel on the headband to act as a visor.

3. The facial sunshield of claim 1 wherein said one piece lens is attached to a headband and hinging means which enables said one piece lens to swivel on the headband and when positioned at the full up position act as a head cap thereby shielding a wearer's head and wearers forehead from sun radiation.

4. The facial sunshield of claim 1 wherein said one piece lens is attached to a headband and hinging means which enables said one piece lens to swivel on said headband and which comprises frictional or ratcheting means to hold the said lens in any rotated position.

5. The facial sunshield of claim 1 wherein said one piece lens is attached to a headband and adjustment means which enables said one piece lens to slide closer or farther from a wearer's face.

6. The facial sunshield of claim 1 wherein said one piece lens is attached to a headband, said headband comprises adjustable strap means connected to said headband for adjustment of said headband to lengthen or shorten said headband relative to a wearer's head size.

7. A facial sunshield comprising a one piece lens which is designed to curve around the top, front, and sides of a wearer's face, said lens sized to substantially cover the forehead, front, and sides of a wearer's face and a wearer's nose, mouth and chin, said lens having a curved upper portion generally designed to follow the angle of a wearer's forehead, said lens having curved side portions generally formed to shield a wearer's cheeks, said lens having a curved bottom portion formed to shield a wearer's mouth and chin generally designed to extend down as far as a wearer's chin, said lens having a curved center portion formed to shield a wearer's eyes and nose, said lens having side edges generally designed to extend to a wearer's jaw line and formed to leave a wearer's ears uncovered, said lens having a top edge designed to extend generally to the top of a wearer's hairline, said lens having tinting for eye comfort, said lens having an ultraviolet radiation blocking coating to protect a wearer's face from harmful ultraviolet radiation, and said lens to be optically corrected whereby a wearer may view through said lens to benefit from the optical correction offered thereby.

8. The facial sunshield of claim 7 wherein said one piece lens is attached to a headband and hinging means which enables said one piece lens to swivel on the headband to act as a visor.

9. The facial sunshield of claim 7 wherein said one piece lens is attached to a headband and hinging means which enables said one piece lens to swivel on the headband and when positioned at the full up position act as a head cap thereby shielding a wearer's head and wearer's forehead from sun radiation.

10. The facial sunshield of claim 7 wherein said one piece lens is attached to a headband and hinging means which enables said one piece lens to swivel on said headband and which comprises frictional or ratcheting means to hold the said lens in any rotated position.

11. The facial sunshield of claim 7 wherein said one piece lens is attached to a headband and adjustment means which enables said one piece lens to slide closer or farther from a wearers face.

12. The facial sunshield of claim 7 wherein said one piece lens is attached to a headband, said headband comprises adjustable strap means connected to said headband for adjustment of said headband to lengthen or shorten said headband relative to a wearer's head size.

* * * * *